(12) United States Patent
Jang et al.

(10) Patent No.: US 7,048,835 B2
(45) Date of Patent: May 23, 2006

(54) SYSTEM AND METHOD FOR ACETIC ACID RECOVERY DURING TEREPHTHALIC ACID PRODUCTION

(75) Inventors: Ji-Young Jang, Plano, TX (US); Hyung-Jin Kim, Suncheon (KR); Kuang Wu, Plano, TX (US)

(73) Assignee: AMT International, Inc., Richardson, TX (US)

( * ) Notice: Subject to any disclaimer, the term of this patent is extended or adjusted under 35 U.S.C. 154(b) by 0 days.

(21) Appl. No.: 10/075,577

(22) Filed: Feb. 12, 2002

(65) Prior Publication Data

US 2003/0150706 A1    Aug. 14, 2003

(51) Int. Cl.
B01D 3/36      (2006.01)
C07C 51/46     (2006.01)
C07C 53/08     (2006.01)

(52) U.S. Cl. .............. 203/16; 203/2; 203/60; 203/DIG. 20; 203/91; 562/607; 562/608

(58) Field of Classification Search .......... 203/16, 203/87, 60, 2, 14, 91, DIG. 20; 562/608, 562/607
See application file for complete search history.

(56) References Cited

U.S. PATENT DOCUMENTS

| | | | | |
|---|---|---|---|---|
| 1,991,084 A | * | 2/1935 | Dreyfuss | ............... 203/16 |
| 2,111,140 A | * | 3/1938 | Coutor | ............... 203/16 |
| 2,171,549 A | * | 9/1939 | Gordon et al. | ............... 203/16 |
| 2,275,802 A | * | 3/1942 | Othmer et al. | ............... 203/15 |
| 2,317,758 A | * | 4/1943 | Guinot | ............... 203/16 |
| 5,980,696 A | * | 11/1999 | Parten et al. | ............... 203/1 |

FOREIGN PATENT DOCUMENTS

| EP | 0 764 627 A1 | 9/1996 |
|---|---|---|
| EP | 2003137833 | 11/2001 |
| WO | 96/06065 | * 2/1996 |
| WO | 97/29068 | * 8/1997 |
| WO | WO 98/45239 | 4/1998 |
| WO | WO 2004/002933 A1 | 5/2003 |

OTHER PUBLICATIONS

PCT Notification of Transmittal of the International Search Report or the Declaration mailed Mar. 4, 2004, re PCT/US 03/25320 filed Aug. 12, 2003 (7 pages).

* cited by examiner

Primary Examiner—Virginia Manoharan
(74) Attorney, Agent, or Firm—Baker Botts L.L.P.

(57) ABSTRACT

A distillation system and method for recovering acetic acid from a feed stream containing acetic acid and water stream generated during terephthalic acid production. The invention includes a dehydration column utilizing azeotropic distillation to recover the acetic acid in conjunction with a condenser system to recover the energy.

8 Claims, 6 Drawing Sheets

SYSTEM AND METHOD FOR ACETIC ACID RECOVERY DURING TEREPHTHALIC ACID PRODUCTION

BACKGROUND OF THE INVENTION

The invention relates to chemical processes used in the distillation of industrial chemicals. More particularly, the invention is directed to the recovery of acetic acid used during the production of terephthalic acid.

Terephthalic acid is useful in a diverse variety of industrial applications and chemical processes. For example, terephthalic acid is starting material for producing polyesters including plastic and Dacron™ polyester used in textile and container production. Polyethylene terephthalate (PET) is a form of polyester or Mylar™ that is an extremely tough resin and useful in many industrial and consumer applications. Soft drink and water bottles are made from this resin in addition to plastic jars and clamshell packages used in consumer good transport and food distribution.

Terephthalic acid is typically produced by a reaction of paraxylene with molecular oxygen in the presence of catalysts. During the production process, acetic acid is used as a solvent of terephthalic acid. The acetic acid becomes diluted in water during the oxidation in a reactor section of a terephthalic acid plant in the production cycle. A portion of the acetic acid and water stream is then sent to a dehydration unit to remove the water generated in the reactor for recycling or waste.

Three different approaches have been employed in the terephthalic acid plants to separate the acetic acid and water so that the acetic acid can be recycled back to the reactor while the water generated by the reaction is sent to the waste water treatment facility for safe processing. One approach is by convention distillation wherein the different boiling point of the components provide for the separation of acetic acid and water. An azeotropic distillation approach utilizes entrainers to form azeotropes with the acetic acid and water providing for a change in energy requirements for processing. Liquid-liquid extraction is a final approach for acetic acid and water separation during the terephthalic acid production.

Distillation has been widely used as a primary unit operation for acetic acid recovery from water. In such processes, one or more towers are utilized to process a number of streams of varying concentrations of acetic acid with the purpose of recovering it for further use in an oxidation step. The products from the distillation tower are a bottom stream of concentrated acetic acid and an overhead stream that ideally would be pure water to minimize the loss of the valuable acetic acid solvent. A more pure overhead water stream would also reduce the burden on downstream waste water treatment facilities thereby preventing accidental chemical spills.

However, the distillation of acetic acid and water is not very efficient due to the highly non-ideal vapor/liquid equilibrium characteristics of the acetic acid/water system. Conventional distillation systems require the use of high number of theoretical stages, i.e., actual trays, and a high reflux ratio, i.e., high energy consumption, to obtain reasonably low levels of acetic acid, typically in the range of 0.5–0.8 wt % in the overhead distilled water. The overhead waste water is subsequently processed to recover certain organic by-products, and then, sent to the waster water treatment facility where any remaining acetic acid will be neutralized and spent.

The use of conventional distillation, therefore, involves high investment cost because of the large dimensions of the required tower and column equipment and a high operating cost because of the high amounts of steam consumption involved. Furthermore, the traditional process scheme does not allow one to economically obtain a distillate completely free of acetic acid. This limitation, in turn, presents operating problems including costs associated with the operation resulting from the acetic acid losses, costs associated with the treatment of the acetic acid in the waste water, limitations of the capacity of the downstream waste water treating facility and environmental problems that are continually increasing because of the ever more rigorous standards for acceptable levels of emission to the environment.

There has been an effort to look for alternatives to minimize the high operating costs associated with the conventional distillation for the separation of acetic acid and water. Chemical processors and companies have resorted to azeotropic distillation involving the addition of selective alkyl acetate, such as the isobutyl acetate (IBA), normal butyl acetate (NBA), normal propyl acetate (NPA) etc., as an entrainer to the dehydration column. The entrainer forms a low boiling azeotrope with water and therefore improves the relative volatility of the separation between the acetic acid and the alkyl-acetate/water azeotrope. This reduces the energy or theoretical stage requirements for the same separation. Compared to the conventional distillation, an azeotropic distillation approach typically reduces the energy (i.e., steam) consumption by 20–40% to the acetic acid/water dehydration column while giving relatively low acetic acid concentration, 300–800 ppm, in the distillated water. The azeotropic distillation column is generally operated at ambient pressure in the terephthalic acid plants in all prior art systems.

Effort has also been reported by the use of liquid-liquid extraction with special extractive agents to recover the acetic acid from the water streams to only contain 0.1 wt % acetic acid to 20% acetic acid. Some of the agents usually used are acetates, amines, ketones and phosphine oxides and mixtures thereof. Once the extraction step is completed, a complicated series of distillation steps are required to recover the acid and to recirculate the extractive agent back to the extraction stage.

In view of such energy waste from the use of traditional distillation systems, what is needed is a distillation system which is energy efficient and produces less waste and unwanted byproducts. The system should also recycle both energy and initial products in a environmentally friendly manner. The distillation system and process should also be easily modifiable to existing chemical process systems to enhance current and existing plants. Moreover, the recovery system should be easy to install without large capital expenditures.

For these reasons, it would be desirable for a distillation system for recovering acetic acid to use less energy, generate energy for other uses within the plant. The system should save raw chemicals and material, result in less acetic acid runoff in waste water and save money. Such systems and methods should also be applicable in a wide variety of chemical processes on a wide range of industrial chemicals. The system should also be simple and less expensive to manufacture while being compatible with conventional systems and processes.

SUMMARY OF THE INVENTION

A distillation system is disclosed for recovering acetic acid from water during terephthalic acid production comprising a dehydration column with an overhead section wherein the overhead section includes a condenser or steam generator. The dehydration column has at least one input feed stream containing an acetic acid and water mixture produced during the production of the terephthalic acid where the acetic acid is a solvent for the production and water is a byproduct of the reaction producing the terephthalic acid.

The dehydration column has an entrainer for the azeotropic distillation of the terephthalic acid. In one embodiment, the entrainer is N-butyl acetate. In another embodiment, the entrainer is I-butyl acetate or a mixture of N-butyl acetate and I-butyl acetate. The distillation column has an overhead pressure of at least 1.2 kg/cm² abs. but may be greater than 1.2 kg/cm² abs.

The output bottom stream of the column has a higher acetic acid concentration that the input feed stream.

The distillation system further has a condenser for separating the acetic acid from the water. The output overhead vapor stream of the column has a lower dilute acetic acid concentration than the at least one input feed stream. The condenser condenses a vapor from the overhead of the dehydration column to generate a low pressure steam. The low pressure steam generated has a pressure of at least 0.6 kg/cm² abs but can reach pressures of greater than 2.0 kg/cm² abs.

A distillation method is also disclosed for recovering acetic acid from water during the production of terephthalic acid. The method comprises the steps of providing an input feed stream of water containing acetic acid and distilling the input feed stream in an azeotropic dehydration column having an overhead into a vapor stream. The vapor stream is entrained utilizing N-butyl acetate or I-butyl acetate or a combination thereof. The vapor stream is then condensed to separate acetic acid from water output a bottom stream having a higher acetic acid concentration than the input feed stream and an output overhead stream having a more dilute acetic acid concentration than the input feed stream.

The present invention is a further improvement of the azeotropic distillation process to separate the acetic acid from water in the terephthalic acid (PTA) plant while generating steam via energy recovery. The invention uses either isobutyl acetate (IBA) or, normal butyl acetate (NBA) or their mixtures as an entrainer in the acetic acid distillation column at an overhead operating pressure of 1.3 kg/cm² abs. or higher. The invention includes a steam generation system on top of the dehydration column to recover energy in the form of steam by condensing the overhead vapor leaving the dehydration column and generating a low pressure steam at 0.6–2.0 kg/cm² abs. for various downstream uses. Based on the conventional distillation devices, the acetic acid content in the overhead water can be reduced to approximately 300–800 ppm typical from over 7000 ppm. Further reduction of acetic acid content (to 150 ppm or less) can be achieved by the use of higher performance mass transfer equipment such as multiperforated valves and high capacity trays and downcomers in the column without the expense of additional steam consumption.

Utilizing existing mass transfer devices and equipment within existing plants with existing specifications and separation requirements, the present invention significantly reduces the reboiler duty (i.e., steam consumption) required for the separation. When compared to conventional distillation, the present system and method typically requires 20–40% lower energy than that of conventional distillation processes. Combined with substantially lower energy consumption during the acetic acid/water separation, the present invention significantly reduces the acetic acid in the overhead water, typically, from 0.5–0.8 wt % to 300–800 ppm, or even lower.

The invention is most advantageous when applied to revamp or replacement acetic acid dehydration columns using conventional distillation. Not only is the energy consumption drastically reduced, the acetic acid loss during distillation is significantly reduced before waste water processing. Some energy is recovered through steam generation and helps reduce the operating costs and loads on existing waste water treating facilities.

This invention relates to a new method for recovering acetic acid, which is the solvent typically used in the production of terephthalic acid and is also a recoverable waste stream in other important industrial processes. The system and method also provides a significant reduction in the total net energy consumption of a plant and allows for an increase in capacity for existing plants. A plant according to the present invention generates a 0.6 kg/cm abs. or higher pressure of steam for use additional power generation and use within the plant. The improved terephthalic acid plant also minimizes the waste water treating facility requirements and eliminates organics emission problems currently existing in most terephthalic acid production plants. In one embodiment, the invention provides a modification to existing acetic acid distillation systems in conjunction with an azeotropic distillation system to be operated at higher than ambient operating pressure thus saving energy and recovering more acetic acid.

The invention also offers its economic benefits in new terephthalic acid plant construction where the overall energy consumption of the invention is the lowest among all current and prior art methods. The present invention is also particularly useful during revamps wherein existing plants are updated with new components during retrofitting or regular maintenance. The system and method may also be designed into new terephthalic acid plant construction.

These, and other, goals and embodiments of the invention will be better appreciated and understood when considered in conjunction with the following description and the accompanying drawings. It should be understood, however, that the following description, while indicating preferred embodiments of the invention and numerous specific details thereof, is given by way of illustration and not of limitation. Many changes and modifications may be made within the scope of the invention without departing from the spirit thereof, and the invention includes all such modifications.

DESCRIPTION OF SPECIFIC EMBODIMENTS

The invention arose out of an observation that, a large amounts of energy was expended within the system for the production of terephthalic acid. In addition to the energy expenditures, minimal to no recycling was occurring where solvents such as acetic acid were not recovered and were sent to waste water treatment facilities thereby increasing the energy requirements by requiring further processing outside the scope of the plant system.

Typically, industrial chemical such as terephthalic acid is produced during multiple fractionation stages where heavier liquids are distilled with lighter vapors. A distillation column is used which comprises a cylindrical tower housing with multiple tower internals to promote the interaction between the vapor and liquid.

Conventional tower internals include sieve and valve trays, random and structured packings or any combination thereof. Preferably, high performance tower internals will be used in the production of terephthalic acid according to the present invention. This includes advance dispersion valves such as perforated valves as disclose in U.S. Pat. No. 6,145,816, of which the entire disclosure is incorporated herein by reference. Multiple downcomer and capacity increasing bubble promoters may also be used to enhance the efficiency and capacity of the distillation column.

Figure 1:
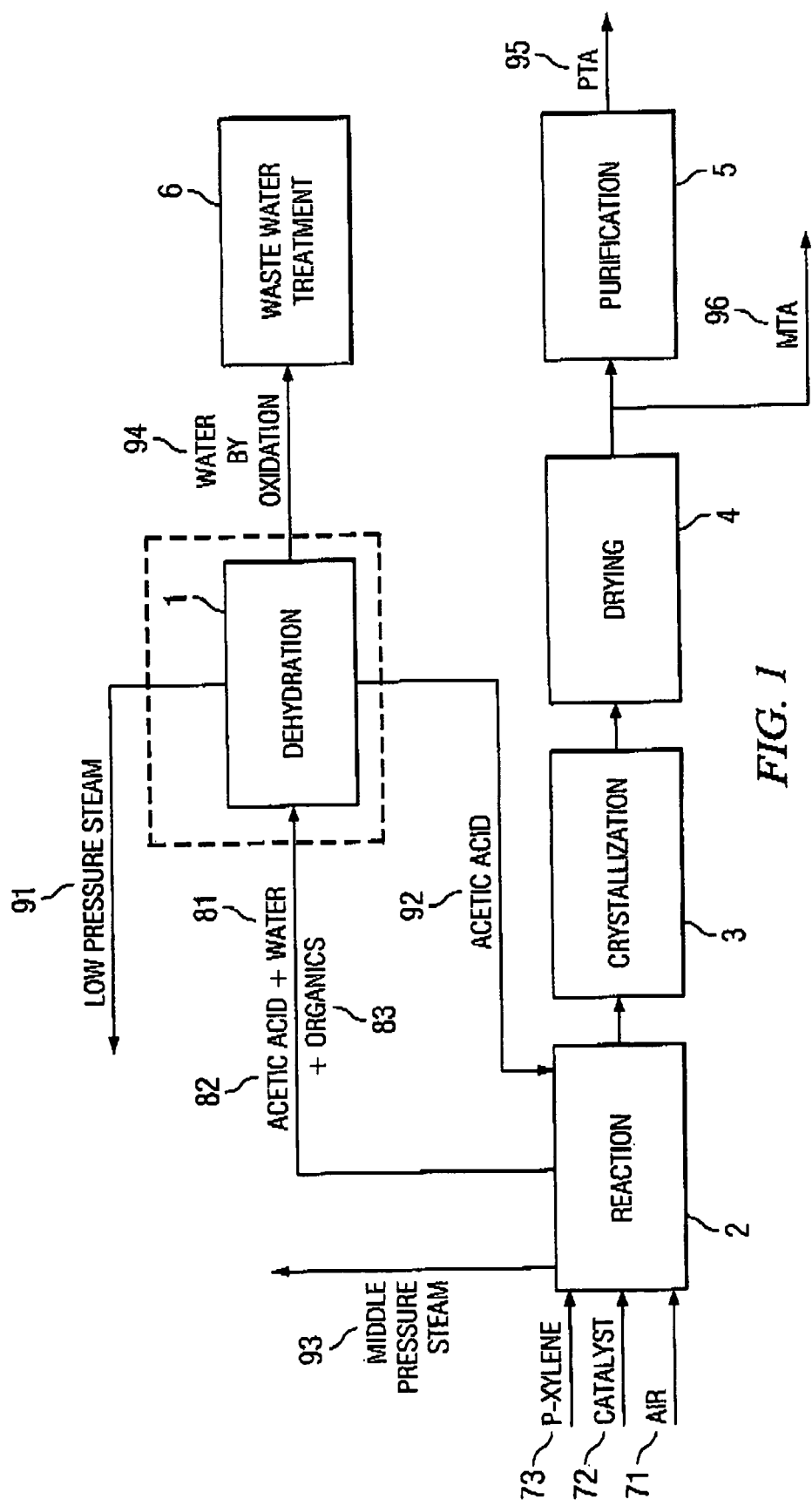
FIG. 1 is a block diagram outlines various process units in a typical plant during terephthalic acid production.

Turning now to the figures where like numerals depict similar components, FIG. 1 is a schematic block flow diagram of a typical terephthalic acid process plant. The major sections of the plant consist of reaction 2, crystallization 3, drying 4, purification 5, dehydration 1 sections or units. A waste water treatment facility 6 is typically the final component for processing in the terephthalic plant.

The feedstock or inputs comprise paraxylene 73 and molecular oxygen (i.e., air 71) along with a catalyst 71 are fed into the reaction section 2 or reactor. Terephthalic acid 95 (PTA) is a product of the reactor. The product and water are produced according to the following chemical reaction:

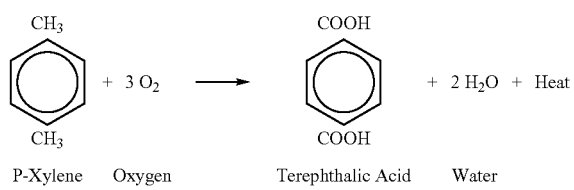

P-Xylene  Oxygen  Terephthalic Acid  Water

The terephthalic acid product is sent to crystallization 3, drying 4 and purification 5 units for further downstream processing to produce purified terephthalic acid 95. The water 81 generated from the reaction and the solvent used in the reaction, i.e., the acetic acid 82, are sent to the dehydration section to recover the acetic acid 92 and return it to the reaction section for reuse. Middle grade terephthalic acid 96 (MTA) cal also be produced and recovered before further purification into terephthalic acid 95 in the reaction. The water 94 is then sent to a waste water treatment facility for disposal.

Typically, the heat generated in the above exothermic reaction to produce the terephthalic acid is recovered by the generation of the middle pressure steam 93. The middle pressure steam is generally used in the dehydration section. The present invention applies to the dehydration section.

Figure 2:
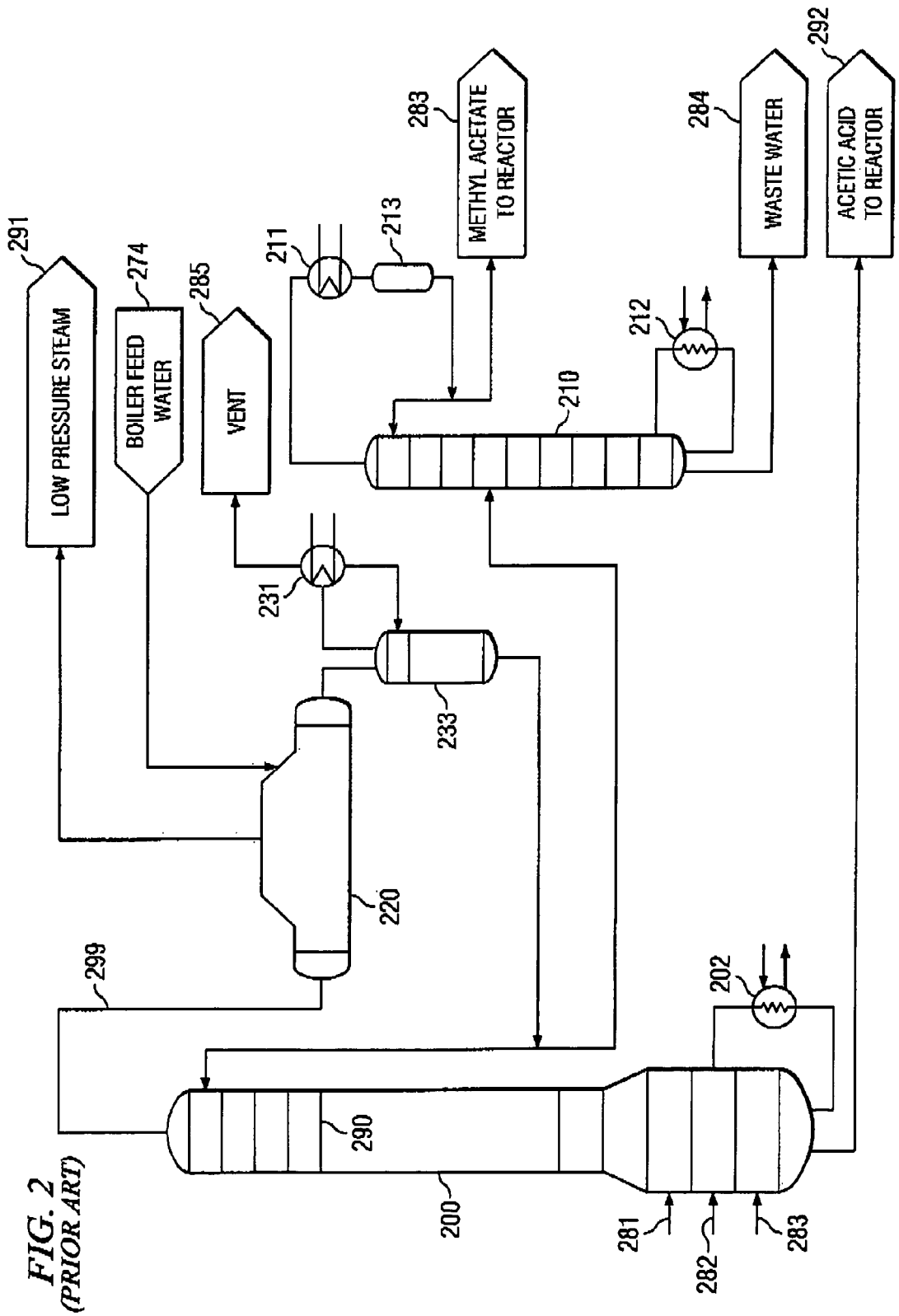
FIG. 2 illustrates a flow diagram of an acetic acid dehydration column using conventional distillation typically found in prior art terephthalic acid plants.

FIG. 2 illustrates a typical flow diagram using a conventional distillation method for acetic acid dehydration in the dehydration section of the terephthalic acid production plant. The conventional distillation system incorporates a steam generator to recover some steam for reuse.

Dehydration column 200 typically includes trays 290 and a reboiler 202. Water streams 281 containing acetic acid solvent 282 and a small amount of organic by-product 283, methyl acetate, are fed to the dehydration column 200 which typically consists of 70–90 distillation trays 290. Acetic acid 292, typically at 92–95 wt % concentration, is recovered from the bottom of the dehydration column 200 and returned to the reaction section Water, organic by product, methyl acetate and any unrecovered acetic acid (typically 0.5–0.8 wt % in concentration) exit the top of column 200 as overhead vapor 299. The overhead vapor is then condensed by overhead condenser 220 with boil feed water 274. Overhead condenser 220 produces low pressure steam 291 during condensation to recover some energy to be recycled into the plant for various uses. Typically, a conventional dehydration column generates low pressure steam (typically 0.6–0.7 kg/cm$^2$ g) at the top of the column.

The resulting condensate of overhead vapor 299 is then fed to a reflux drum 233. A secondary condenser 231 further condenses the condensate with non-condensable vapor vented through vent 285. A portion of the resulting reflux is recycled back to column 200 as reflux.

The remaining portion of the reflux is fed downstream to methyl acetate column 210 to separate the organic by-product, methyl acetate 283 as the overhead product and the water and the acetic acid as the bottom product. Column 210 has a condenser 211, a receiver or reflux drum 213 and a reboiler 212. The water stream 284 containing the acetic acid is then sent to the wastewater treatment facility for disposal. The methyl acetate 283 is fed back to the reactor for recycling.

Figure 5:
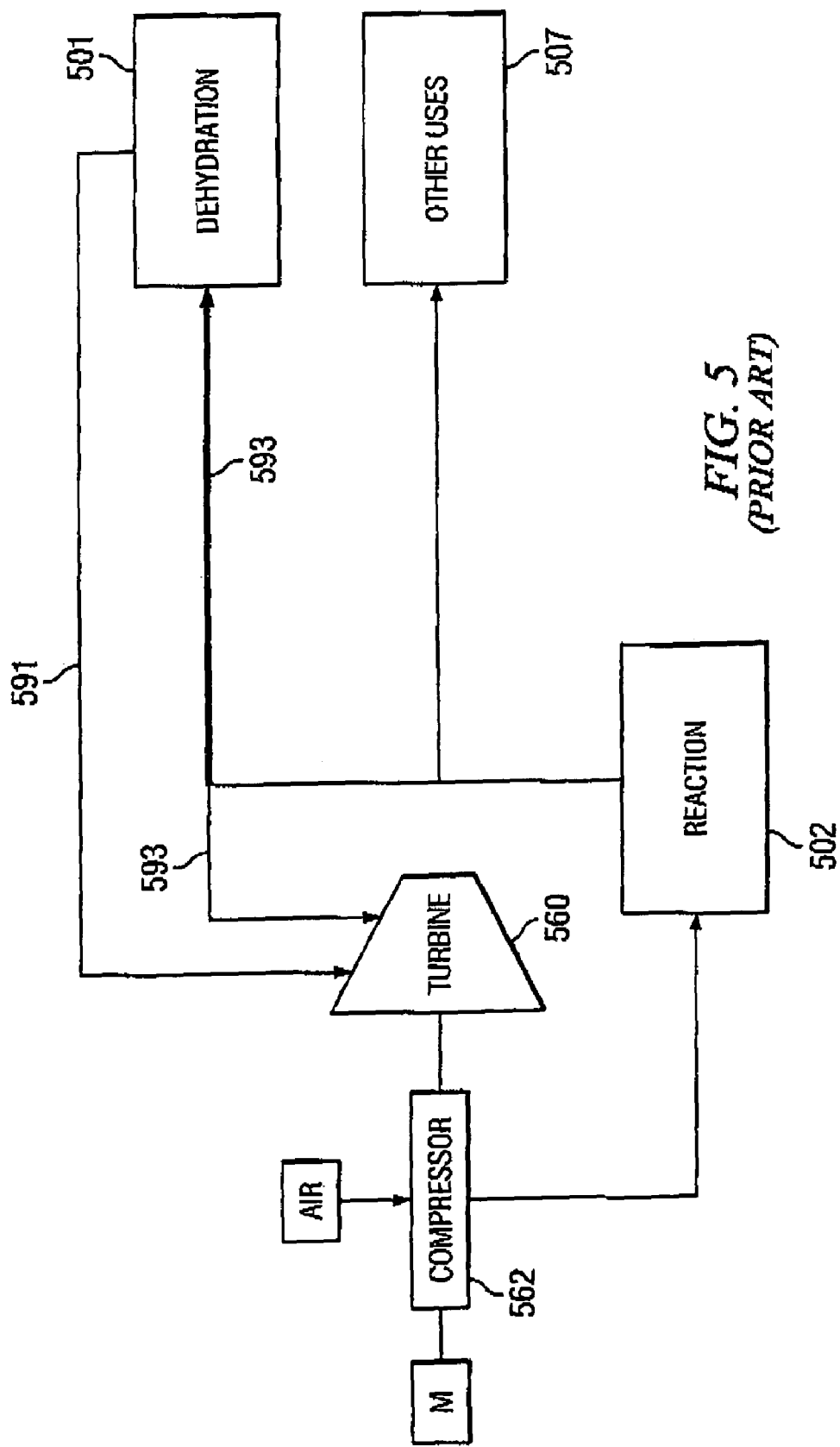
FIG. 5 shows a flow diagram of the steam generated utilizing a conventional distillation process.

Typically, a portion of the middle pressure steam generated in the reaction section provides a heat source to the reboiler 202 of the dehydration column 200 for use during the acetic acid/water separation. The balance of the steam is used in power generation or other purposes as illustrated in FIG. 5. Approximately 50% of the middle pressure steam generated is used for the distillation needs in the dehydration section for this conventional distillation method.

Figure 3:
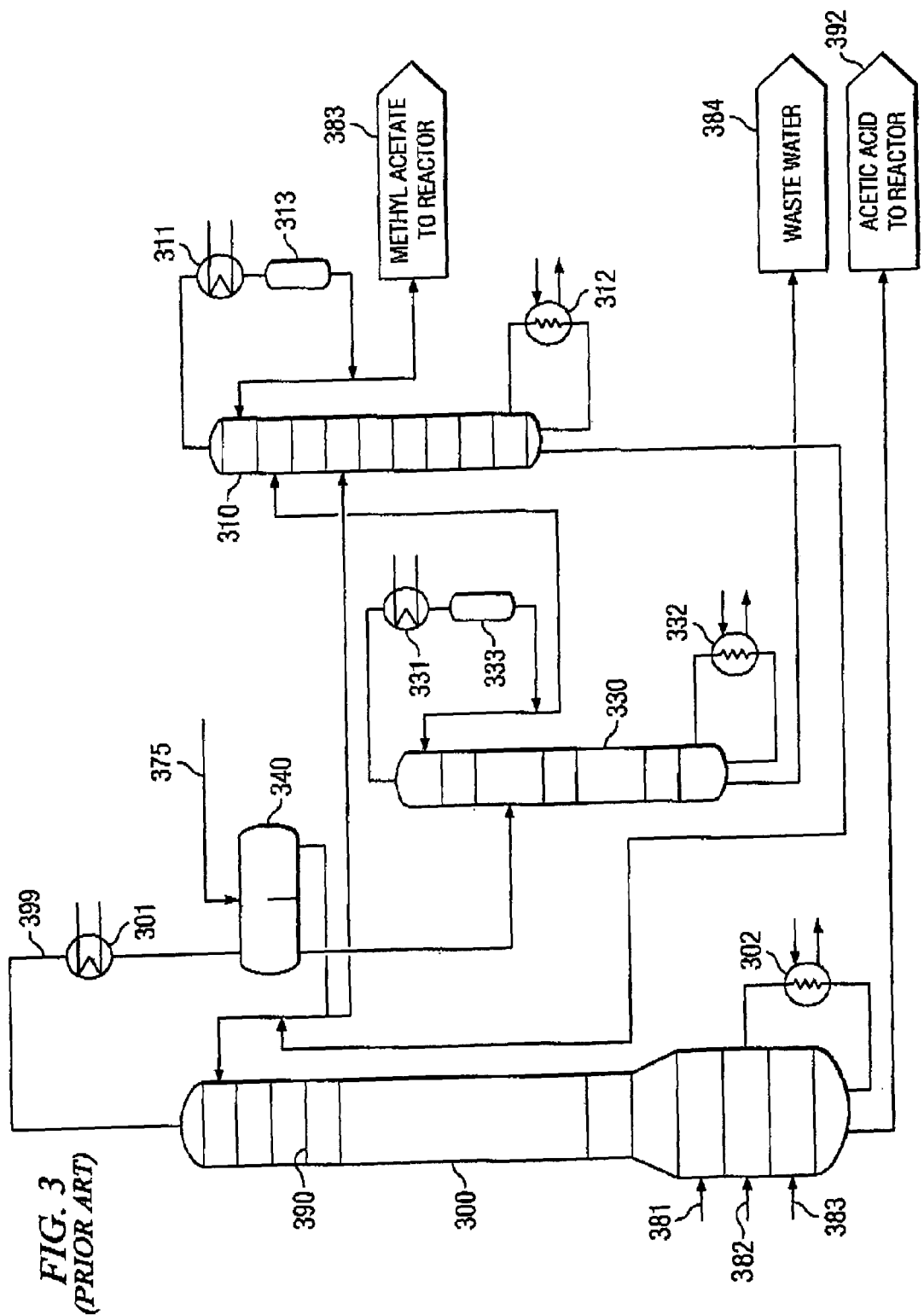
FIG. 3 shows a flow diagram of an acetic acid dehydration column using a typical azeotropic distillation under ambient operating pressure in terephthalic acid plants.

FIG. 3 illustrates a typical flow diagram using prior art azeotropic distillation with entrainers such as isobutyl acetate (IBA) or normal butyl acetate (NBA) in the dehydration section of a typical terephthalic acid plant.

Water streams 381 containing acetic acid solvent 382 and a small amount of organic by-product 383, methyl acetate, are fed into the dehydration column 300. Column 300 has a condenser 301 and a reboiler 302. Typically, dehydration column 300 consists of 60–70 distillation trays 390 operating at or near ambient pressure. Acetic acid 392, typically at 92–95 wt % of concentration, is produced from the bottom of the dehydration column 300 and returned to the reaction section. The water, by forming a low-boiling azeotrope, along with trace amounts of unrecovered acetic acid and a small amount of reaction by-product, methyl acetate, exit the top of the column as overhead vapor 399. An azeotrope is a mixture of pure components that has a constant boiling point and cannot be easily separated by conventional distillation. The boiling point of the azeotrope is lower than the boiling points of either of the two pure components.

The overhead vapor 399 is then condensed and fed into decanter 340. The resulting liquid condensate formed from the overhead vapor 399 forms two phases, an organic phase and a water phase. The organic phase and acetic acid is combined with an entrainer such as IBA or NBA from entrainer makeup 375 in decanter 440. A portion of the organic phase containing the entrainer and organic by-product with acetic acid is recycled back to the column 300 as the reflux.

The remaining portion of the organic phase is fed downstream to methyl acetate column 310 to separate the organic by-product, methyl acetate from the entrainer. Methyl acetate column 310 is preferably a distillation column with trays 390. Column 310 has a condenser 311, a receiver or reflux drum 313 and a reboiler 312. Methyl acetate 383 is recovered in the overhead and recycled to the reactor section. The entrainer is a bottom product of methyl acetate column 310 and recycled back to the decanter 340.

The water phase of the decanter 340 containing water, entrainer, methyl acetate that is dissolved in the water phase and a trace amount of acetic acid (typically 300–800 ppm) is then fed to a downstream stripper column 330 to separate the methyl acetate and acetic acid. Stripper column 330 has a condenser 331, a receiver or reflux drum 333 and a reboiler 332. Methyl acetate is separated as the overhead product which is then sent to the methyl acetate column 310 to separate the methyl acetate and the entrainer. The water product 384 from the bottom product of column 330 containing a small amount of unrecovered acetic acid is then sent to the waste water treatment facility for disposal.

There are two primary advantages of azeotropic distillation over conventional distillation, namely, 1) lower the energy (i.e. steam) consumption by 20–40% and 2) lower acetic acid loss to waste water treating facility from 0.5–0.8 wt % in the waste water. Comparatively, the acetic acid loss is typically 300–800 ppm with the azeotropic distillation versus 7000–7500 ppm for conventional distillation.

Conventional prior art azeotropic distillation dehydration towers in terephthalic acid production plants are operated at ambient operating pressure. Due to the low azeotropic boiling temperature, heat recovery from the top of the dehydration column is not feasible, therefore, no steam generation system are used during typical azeotropic distillation for acetic acid dehydration the terephthalic acid plants. Thus, no energy is recovered for other uses thereby increasing the total net energy consumption within the plant.

Figure 6:
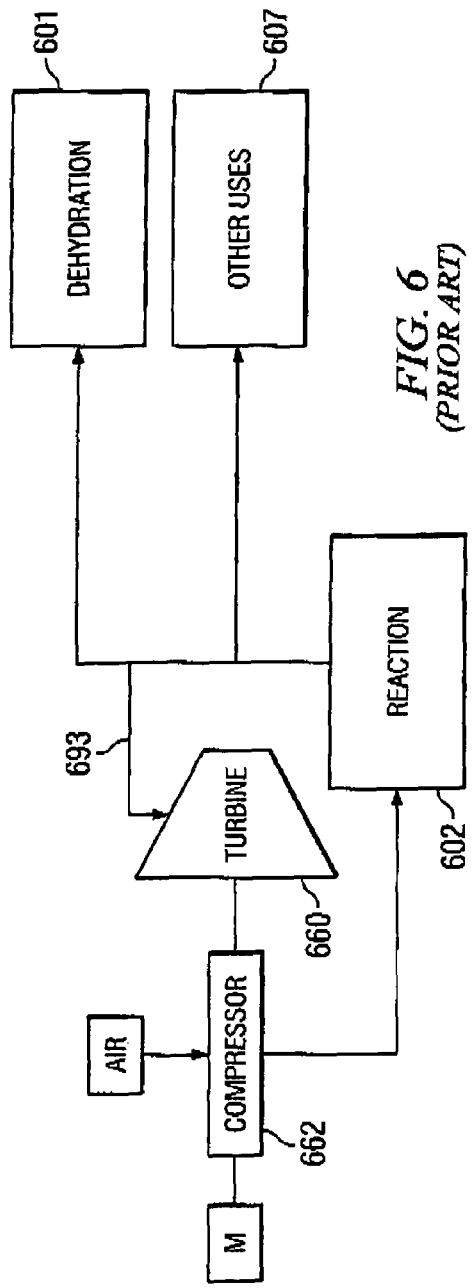
FIG. 6 is a flow diagram of the steam generation from only the reaction section and its usage in a typical terephthalic acid plant.

Typically, a portion of the middle pressure steam generated in the reaction section (not shown) provides a heat source to the reboiler 302 of the dehydration column 301 for the required acetic acid/water separation. The balance of the steam is used in power generation or other purposes as illustrated in FIG. 6. Only approximately thirty percent (30%) of the middle pressure steam generated is used for distillation needs in the dehydration section during prior art azeotropic distillation.

Figure 4:
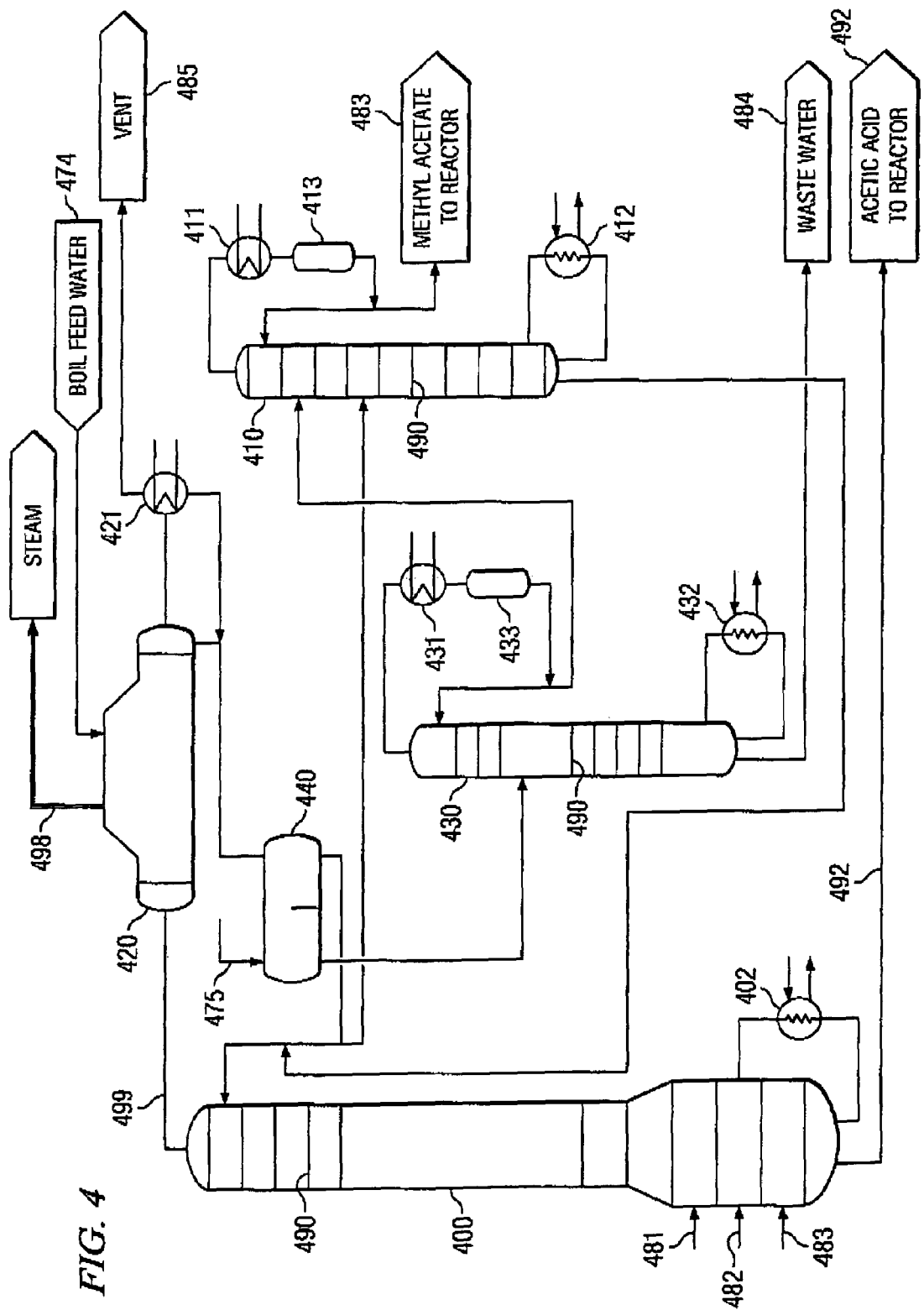
FIG. 4 is a flow diagram of an acetic acid recovery system according to the present invention, in which an azeotropic distillation column is equipped with a condenser which is an overhead steam generation system to generate low pressure steam.

FIG. 4 illustrates the flow diagram of the subject invention employing both the azeotropic distillation, with entrainers to form azeotropes and a steam generation/heat recovery system in the dehydration section of the terephthalic acid plant. The present invention further improves azeotropic distillation systems by generating steam during the separation of acetic acid from water in the distillation phase of terephthalic acid production. Isobutyl acetate (IBA) or normal butyl acetate (NBA) or their mixtures is used as an entrainer in the acetic acid dehydration column. The column has an overhead operating pressure of 1.3 kg/cm$^2$ abs. or higher. A steam generation system is located on top of the dehydration column to recover the steam energy by condensing the overhead vapor column. The steam is a low pressure steam of about 0.6–2.0 kg/cm$^2$ abs. In another embodiment, the steam is a low pressure steam from 0.7–2.0 kg/cm$^2$ abs. Acetic acid is recovered from the system in the amount of 300–800 ppm.

A system according to the present invention incorporated into an existing mass transfer plant significantly reduces reboiler duty (i.e. steam consumption) required for the separation process. Energy consumption is lowered 20–50% compared to prior art methods while maintaining low acetic aid loss in waste water to 0.5–0.8 wt % to 300–800 ppm or lower. When combined with advanced mass transfer devices such as perforated valves, advanced downcomers and tower internals or any equivalent high performance equipment, acetic acid loss may be reduced to only 150 ppm or less.

Turning now to FIG. 4, water streams 481 containing acetic acid solvent 482 and a small amount of organic by-product 483, methyl acetate, are fed into a dehydration column 400. In one embodiment, dehydration column 400 comprises at least 60 distillation trays 490. Column 400 is operated at higher operating pressure greater than at least 1.3 kg/cm$^2$ abs. at the top of the dehydration column 400. Acetic acid 492, typically at a concentration of 92–95 wt %, is produced from the bottom of the dehydration column 400 and returned to the reaction section. Water, by forming a low-boiling azeotrope, along with trace amounts of unrecovered acetic acid and a small amount of reaction by-products including methyl acetate exit the top of the column 400 as overhead vapor 499. The overhead vapor 499 is then condensed by steam generator or overhead condenser 420 which produces low pressure steam 498. Overhead condenser 420 has a secondary condenser 421 which further condenses the overhead vapor 499 with any non-condensable vapor vented through vent 485. Boil feed water 474 is provided to the system to generate the steam necessary to support the various units such as the overhead condenser.

The liquid condensate formed from the overhead vapor 499 is then fed into decanter 440 and forms two liquid phases, an organic phase and a water phase. The organic phase and acetic acid is combined with an entrainer of IBA or NBA from entrainer make up 475 in decanter 440. A portion of this mixture is recycled back to column 400 as reflux.

The remaining portion of the organic phase is fed downstream to methyl acetate column 410 to separate the organic by-product, methyl acetate from the entrainer. Methyl acetate column 410 is preferably a distillation column with trays 490. Column 410 has a condenser 411, a receiver or reflux drum 413 and a reboiler 412. Methyl acetate 483 is recovered in the overhead and recycled to the reactor section. The entrainer is a bottom product of methyl acetate column 410 and recycled back to the decanter 440.

The water phase of the decanter 440 containing water, entrainer, methyl acetate that is dissolved in the water phase and a trace amount of acetic acid (typically 300–800 ppm) is then fed to a downstream stripper column 430 to separate the methyl acetate and acetic acid. Stripper column 430 preferably is a distillation column with trays 490. Column 430 has a condenser 431, a receiver or reflux drum 433 and a reboiler 432. Methyl acetate is separated as the overhead product which is then sent to the methyl acetate column 410 to separate the methyl acetate and the entrainer. The water product 484 from the bottom product of column 430 containing a small amount of unrecovered acetic acid is then sent to the waste water treatment facility for disposal.

While the higher column operating pressure disclosed in the present invention is not significantly different from the energy consumption and acetic acid losses when compared to prior art azeotropic distillation systems operating at ambient pressure, the present invention generates useful low pressure steam within condenser 420 at a pressure of 0.6–2.0 kg/cm² because of the higher initial operating pressure. Unlike prior art azeotropic distillation, the present system and method allows the overhead temperature in the azeotropic dehydration column to be high enough for the generation of the low pressure steam 498 that can be used for power generation and/or other uses. The steam generation, though at low pressure, is not feasible within prior art azeotropic distillation systems used in the terephthalic acid plants.

Figure 7:
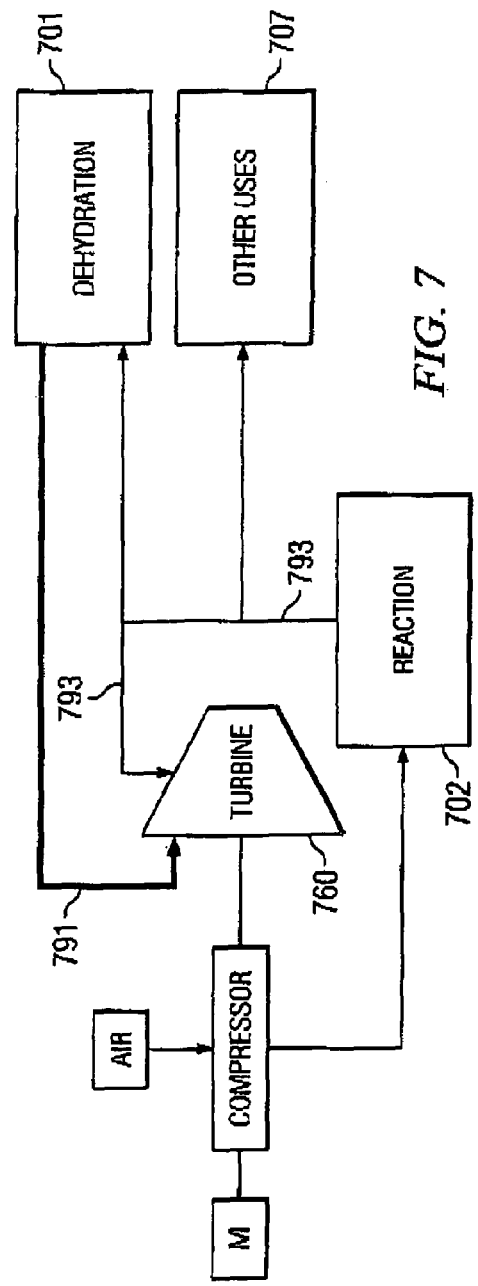
FIG. 7 illustrates a flow diagram of the generation of steam from the reaction section in combination from the steam generated during the dehydration process during terephthalic acid production.

Preferably, a portion of the middle pressure steam generated in the reaction section (not shown) provides a heat source to the reboiler 402 of the dehydration column 400 for the required acetic acid/water separation. The balance of the steam is used in power generation or other purposes as illustrated in FIG. 7. Only less than approximately thirty percent (30%) of the middle pressure steam generated is used for distillation needs in the dehydration section during prior art azeotropic distillation.

The key advantages for the present invention over conventional distillation methods and azeotropic distillation schemes in terephthalic acid plants provide benefits including:

1. lower energy (i.e. steam) consumption and savings of at least 20–40%;
2. lower acetic acid loss to the waste water treating facility from 0.5–0.8 wt % in the waste water in conventional distillation versus 300 ppm–800 ppm or lower in azeotropic distillation; and
3. recovery of total net energy by generating low pressure steam of at least 0.6–2.0 kg/cm² abs. for power generation or other uses in the plant.

Having generally described the invention, a further understanding can be obtained by reference to the following example, which is provided herein for purposes of illustration only, and are not intended to be limiting in any manner unless otherwise specified.

EXAMPLE

In a typical 350,000 MTA terephthalic acid production plant, various acetic acid dehydration methods, namely, conventional distillation, azeotropic distillation at ambient operating pressure and the invention are compared. The typical design and operating benefits of the various methods are summarized in the table below:

|  | Conventional distillation | Azeotropic Distillation (Prior Art) | Invention (case 1) | Invention (case 2) |
|---|---|---|---|---|
| Entrainer used | none | Iso-Butyl Acetate | N-Butyl Acetate & Iso-Butyl Acetate | N-Butyl Acetate & Iso-Butyl Acetate |
| PTA Production | 350,000 | 350,000 | 350,000 | 350,000 |
| Typical No. of trays in Dehydration Column | 90 | 70 | 70 | 90 |
| Pressure of Steam generated from Reaction Section (kg/cm2 abs.) | 6 and 1.5 | 6 and 1.5 | 6 and 1.5 | 6 and 1.5 |
| Middle pressure steam (6 kg/cm2 abs.) consumption in Dehydration Section (T/hr) | 60 | 42 | 42 | 36 |
| Pressure of Steam generated from Dehydration Section (kg/cm2 abs.) | 0.6–0.7 | none | 0.6–2.0 | 06–2.0 |
| Amount of Steam generated from the Dehydration section (T/hr) | 52 | none | 38 | 34 |
| Typical Acetic Acid conc. to Waste Water treating, ppm | 7000 | 300 | 300 | 300 |
| Waste Water flow rate to WWT, Ton/hr | 13 | 13 | 13 | 13 |
| Total Acetic Acid loss to WWT,Ton/year | 728 | 31.2 | 31.2 | 31.2 |

As illustrated in the table above, a dehydration column using conventional distillation with 90 fractionation trays consumes the highest middle pressure steam amount at 60 T/hour during dehydration thus using more total energy. This steam use and consumption is greater than both conventional azeotropic distillation and the present invention. However, the energy consumed in dehydration is typically recovered by the generation of low pressure steam from the overhead section of the dehydration column. Consequently, the acetic acid loss by using conventional distillation method is substantially higher than both that of the conventional azeotropic distillation or the present invention.

It is theoretically possible to increase the column reflux or number of fractionation trays to further reduce the acetic acid loss in the water stream during conventional distillation. However, it is not economically justifiable due to the exponentially increasing costs in both higher energy consumption and/or higher capital investments by requiring more raw materials for column construction.

In comparison, in a dehydration column using azeotropic distillation equipped with 70 fractionation trays, energy consumption is approximately seventy (70%) of that of the energy consumption during conventional distillation. Additionally, acetic acid loss is substantially reduced when compared to that of conventional distillation as demonstrated above. The disadvantage of this approach is that, due to lower operating pressure of the azeotropic distillation, it is not feasible to recover the energy through steam generation during dehydration.

In contrast, the present invention offers not only the lowest energy consumption but also provides the lowest acetic acid loss. In one embodiment, the terephthalic acid production system and method according to the present invention is equipped with seventy (70) fractionation trays. In another embodiment, the system comprises ninety (90) fractionation trays.

Moreover, due to elevated operating pressures at the top of the dehydration column, the present invention also recovers a greater amount of energy than that of prior art systems by generating a greater low pressure steam in addition to the middle pressure steam simultaneously. This low pressure steam can be recycled and returned to the system for many other uses within the plant thus globally saving energy.

As shown in either embodiment of the present invention, the total acetic acid loss remains low as in typical azeotropic distillation and in comparison to conventional distillation. The invention combines both the benefits of conventional distillation and azeotropic distillation in a novel way to provide substantial economical benefits over prior art systems and methods. The energy savings and recovery of more raw materials and chemicals may be used both the new plant constructions and the revamp projects.

Turning now to FIGS. 5–7, steam flow and generation within a terephthalic acid plant are shown under various operating schemes. FIG. 5 depicts a flow of steam generated by a steam generation system in conventional distillation for use within the plant. The system generates both middle pressure steam 593 and low pressure steam 591.

Reaction unit 502 produces middle pressure steam 593 at a pressure of 3.5–5.0 kg/cm g. Most of the middle pressure steam 593 is consumed primarily in the dehydration section 501 for use during acetic acid and water distillation. Middle pressure steam 593 also turns turbine 560 for power generation within the plant for uses such as pushing the compressor 562 and other utility uses 507.

Low pressure steam 591 is generated by the dehydration section 501 at a typical pressure of 0.5–0.8 kg/cm$^2$ abs. during the distillation of acetic acid and water. The low pressure steam 591 is then sent to steam turbine 560 for additional power generation for use within the plant.

In contrast to conventional distillation, FIG. 6 shows the flow of steam generation and usage in a terephthalic acid production plant during azeotropic distillation. The system generates only middle pressure steam 693 at a typical pressure of 3.5–6.0 kg/cm g. Middle pressure steam 693 is produced in the reaction section 602 of the plant and is consumed mainly in the dehydration section 601 for use in acetic acid and water distillation. Steam 693 is also used in turbine 660 for power generation and for the consumption in the crystallization section and other utility uses 607.

Referring to FIG. 7, a steam flow diagram is illustrated according to the system of the present invention. The system generates both middle pressure steam 793 and low pressure steam 791 simultaneously.

Reaction unit 702 produces middle pressure steam 793 at a pressure of 3.5–5.0 kg/cm g. Middle pressure steam 793 is consumed in the dehydration section 701 for use during acetic acid and water distillation. Middle pressure steam 793 also turns turbine 760 for power generation within the plant for uses such as pushing the compressor 762 and other utility uses 707.

Low pressure steam 791 is generated by the dehydration section 701 at a typical pressure of 0.4–2.2 kg/cm$^2$ abs. during the distillation of acetic acid and water. The low pressure steam 791 is then sent to steam turbine 760 for additional power generation for use within the plant.

Thus, a terephthalic acid production plant, distillation system and method according to the present invention provides various advantages over a conventional distillation method and an azeotropic distillation scheme. Lower energy and steam consumption is required in the present system. A higher acetic acid recovery from reaction water such that less acetic acid is lost to be processed at a waste water facility. Additionally, the dehydration of the acetic acid during the terephthalic acid production generates a more useful low pressure steam for power generation or other uses in the plant.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

All publications and patent applications mentioned in this specification are herein incorporated by reference to the same extent as if each individual publication or patent application was specifically and individually indicated to be incorporated by reference.

While the invention has been described with respect to its preferred embodiments, it will be appreciated that other alternative embodiments may be included. For example, with respect to all of the explicitly disclosed embodiments, as well as all other embodiments of the invention, a different distillation system including different tray designs and arrangements may be incorporated. Various other column modifications including multiple dehydration stages and uses of alternate entrainers may be utilized. These and various other modifications can be made to the disclosed embodiment without departing from the subject of the invention.

What is claimed is:

1. A distillation method for recovering acetic acid from water during the production of terephthalic acid, the method comprising;

providing an input feed stream of water containing acetic acid;

separating, in an azeotropic dehydration column having an overhead section, a bottom stream having a higher acetic acid concentration than the input feed stream from an overhead vapor stream having a more dilute acetic acid concentration than the input feed stream, the azeotropic dehydration column operating at greater than ambient pressure;

condensing the vapor stream to generate low pressure steam at a pressure level from 0.7–2.0 kilograms/cm$^2$; and wherein the overhead section has an overhead pressure of at least 1.2 kg/cm$^2$ abs.

2. The distillation method according to claim 1 further comprising entraining the vapor stream using N-butyl acetate.

3. The distillation method according to claim 1 further comprising entraining the vapor stream using I-butyl acetate.

4. The distillation method according to claim 1 further comprising entraining the vapor stream using a mixture of N-butyl acetate and I-butyl acetate.

5. The distillation method according to claim 1 wherein the low pressure steam is greater than 0.7 kg/cm$^2$ but less than or equal to 2.0 kg/cm$^2$.

6. The distillation method according to claim 1 wherein the overhead section has an overhead pressure of greater than 1.2 kg/cm$^2$ abs.

7. The distillation method of claim 1, and further comprising using the low pressure steam for power generation.

8. The distillation method of claim 1, and further comprising directing the low pressure steam to a power generator.

* * * * *